(12) United States Patent
Orbay

(10) Patent No.: US 8,403,967 B2
(45) Date of Patent: Mar. 26, 2013

(54) VOLAR FIXATION SYSTEM AND METHODS OF USING THE SAME

(75) Inventor: Jorge L. Orbay, Coral Gables, FL (US)

(73) Assignee: Biomet C.V., Gibraltar (GI)

( * ) Notice: Subject to any disclaimer, the term of this patent is extended or adjusted under 35 U.S.C. 154(b) by 212 days.

(21) Appl. No.: 12/823,738

(22) Filed: Jun. 25, 2010

(65) Prior Publication Data

US 2010/0268283 A1 Oct. 21, 2010

Related U.S. Application Data

(63) Continuation of application No. 11/181,354, filed on Jul. 14, 2005, now abandoned, which is a continuation of application No. 10/762,695, filed on Jan. 22, 2004, now abandoned, which is a continuation-in-part of application No. 10/315,787, filed on Dec. 10, 2002, now Pat. No. 6,706,046, which is a continuation-in-part of application No. 10/159,611, filed on May 30, 2002, now Pat. No. 6,730,090, which is a continuation-in-part of application No. 09/735,228, filed on Dec. 12, 2000, now Pat. No. 6,440,135, which is a continuation-in-part of application No. 09/524,058, filed on Mar. 13, 2000, now Pat. No. 6,364,882, and a continuation-in-part of application No. 09/495,854, filed on Feb. 1, 2000, now Pat. No. 6,358,250.

(51) Int. Cl.
*A61B 17/88* (2006.01)

(52) U.S. Cl. .................. 606/281; 606/291

(58) Field of Classification Search ........... 606/59, 606/98, 281, 282, 283, 286, 288, 291, 298
See application file for complete search history.

(56) References Cited

U.S. PATENT DOCUMENTS

| | | | |
|---|---|---|---|
| 388,000 A | 8/1888 | Rider | |
| 472,913 A | 4/1892 | Taylor | |
| 1,151,861 A | 8/1915 | Brumback | |
| 2,056,688 A | 10/1936 | Peterka et al. | |
| 2,500,370 A | 3/1950 | McKibbin | |
| 2,526,959 A | 10/1950 | Lorenzo | |
| 3,025,853 A | 3/1962 | Mason | |
| 3,236,141 A | 2/1966 | Smith | |
| 3,489,143 A | 1/1970 | Halloran | |
| 3,645,161 A | 2/1972 | Wesker | |
| 3,709,218 A | 1/1973 | Halloran | |
| 3,717,146 A | 2/1973 | Halloran | |
| 3,741,205 A | 6/1973 | Markolf et al. | |
| 3,842,825 A | 10/1974 | Wagner | |
| 3,939,498 A | 2/1976 | Lee et al. | |
| RE28,841 E | 6/1976 | Allgower et al. | |
| 4,011,863 A | 3/1977 | Zickel | |
| 4,119,092 A | 10/1978 | Gil | |

(Continued)

FOREIGN PATENT DOCUMENTS

CA 2174293 A 10/1997
CH 675531 10/1990

(Continued)

OTHER PUBLICATIONS

M.E. Müller al., 3rd edition (revised), AO Manual for Internal Fixation, Japan, Springer-Verlag Tokyo, Jun. 30, 1997, p. 221.

(Continued)

*Primary Examiner* — Brian Pellegrino
(74) *Attorney, Agent, or Firm* — Gordon & Jacobson, PC

(57) ABSTRACT

A volar fixation system includes a plate intended to be positioned against the volar side of the radial bone. The plate includes holes for receiving fasteners along a fixed axis relative to the plate. The plate is positioned against the radius bone, and a portion of the plate is preliminarily fixed to the radius bone. The fracture is reduced, and a plurality of fasteners are each inserted through a respective plate hole so as to extend immediately below the subchondral bone of the radius bone and is fixed in axial relationship relative to the plate. Together the fasteners form a stabilizing construct that conforms to the concave curvature of the articular surface of the radius bone.

9 Claims, 5 Drawing Sheets

U.S. PATENT DOCUMENTS

| | | | |
|---|---|---|---|
| 4,135,507 A | 1/1979 | Harris | |
| 4,153,953 A | 5/1979 | Grobbelaar | |
| 4,169,470 A | 10/1979 | Ender et al. | |
| 4,172,452 A | 10/1979 | Forte et al. | |
| 4,408,601 A | 10/1983 | Wenk | |
| 4,467,793 A | 8/1984 | Ender | |
| 4,473,069 A | 9/1984 | Kolmert | |
| 4,483,335 A | 11/1984 | Tornier | |
| 4,484,570 A | 11/1984 | Sutter et al. | |
| 4,488,543 A | 12/1984 | Tornier | |
| 4,493,317 A | 1/1985 | Klaue | |
| 4,506,662 A | 3/1985 | Anapliotis | |
| 4,565,193 A | 1/1986 | Streli | |
| 4,651,724 A | 3/1987 | Berentey et al. | |
| 4,712,541 A | 12/1987 | Harder et al. | |
| 4,733,654 A | 3/1988 | Marino | |
| 4,776,330 A | 10/1988 | Chapman et al. | |
| 4,794,919 A | 1/1989 | Nilsson | |
| 4,800,874 A | 1/1989 | David et al. | |
| 4,867,144 A | 9/1989 | Karas | |
| 4,915,092 A | 4/1990 | Firica et al. | |
| 4,923,471 A | 5/1990 | Morgan | |
| 4,943,292 A * | 7/1990 | Foux | 606/286 |
| 4,955,886 A | 9/1990 | Pawluk | |
| 5,006,120 A | 4/1991 | Carter | |
| 5,013,314 A | 5/1991 | Firica et al. | |
| 5,015,248 A | 5/1991 | Burstein et al. | |
| 5,035,697 A | 7/1991 | Frigg | |
| 5,041,113 A | 8/1991 | Biedermann et al. | |
| 5,057,110 A | 10/1991 | Kranz et al. | |
| 5,085,660 A | 2/1992 | Lin | |
| 5,127,912 A | 7/1992 | Ray et al. | |
| 5,151,103 A | 9/1992 | Tepic et al. | |
| 5,190,544 A | 3/1993 | Chapman et al. | |
| 5,197,966 A | 3/1993 | Sommerkamp | |
| 5,201,733 A | 4/1993 | Etheredge, III | |
| 5,275,601 A | 1/1994 | Gogolewski et al. | |
| 5,304,180 A | 4/1994 | Slocum | |
| 5,352,228 A | 10/1994 | Kummer et al. | |
| 5,352,229 A | 10/1994 | Goble et al. | |
| 5,356,253 A | 10/1994 | Whitesell | |
| 5,356,410 A | 10/1994 | Pennig | |
| 5,364,399 A | 11/1994 | Lowery et al. | |
| 5,382,248 A | 1/1995 | Jacobson et al. | |
| 5,437,667 A | 8/1995 | Papierski et al. | |
| 5,458,654 A | 10/1995 | Tepic | |
| 5,472,444 A | 12/1995 | Huebner et al. | |
| 5,484,438 A | 1/1996 | Pennig | |
| 5,486,176 A | 1/1996 | Hildebrand et al. | |
| 5,527,311 A | 6/1996 | Procter et al. | |
| 5,531,745 A | 7/1996 | Ray | |
| 5,531,746 A | 7/1996 | Errico et al. | |
| 5,536,127 A | 7/1996 | Pennig | |
| 5,549,612 A | 8/1996 | Yapp et al. | |
| 5,558,674 A | 9/1996 | Heggeness et al. | |
| 5,578,035 A | 11/1996 | Lin | |
| 5,586,985 A | 12/1996 | Putnam et al. | |
| 5,591,168 A | 1/1997 | Judet et al. | |
| 5,601,553 A | 2/1997 | Trebing et al. | |
| 5,603,715 A | 2/1997 | Kessler | |
| 5,607,426 A | 3/1997 | Ralph et al. | |
| 5,662,655 A | 9/1997 | Laboureau et al. | |
| 5,665,086 A | 9/1997 | Itoman et al. | |
| 5,665,087 A | 9/1997 | Huebner | |
| 5,665,089 A | 9/1997 | Dall et al. | |
| 5,669,915 A | 9/1997 | Caspar et al. | |
| 5,676,667 A | 10/1997 | Hausman | |
| 5,709,682 A | 1/1998 | Medoff | |
| 5,709,686 A | 1/1998 | Talos et al. | |
| 5,718,705 A | 2/1998 | Sammarco | |
| 5,728,099 A | 3/1998 | Tellman et al. | |
| 5,733,287 A | 3/1998 | Tepic et al. | |
| 5,749,872 A | 5/1998 | Kyle et al. | |
| 5,766,174 A | 6/1998 | Perry | |
| 5,772,662 A | 6/1998 | Chapman et al. | |
| 5,776,194 A | 7/1998 | Mikol et al. | |
| 5,785,711 A | 7/1998 | Errico et al. | |
| 5,807,396 A | 9/1998 | Raveh | |
| 5,851,207 A | 12/1998 | Cesarone | |
| 5,853,413 A | 12/1998 | Carter et al. | |
| 5,879,350 A | 3/1999 | Sherman | |
| 5,931,839 A | 8/1999 | Medoff | |
| 5,935,128 A | 8/1999 | Carter et al. | |
| 5,938,664 A | 8/1999 | Winquest et al. | |
| 5,941,878 A | 8/1999 | Medoff | |
| 5,951,557 A | 9/1999 | Luter | |
| 5,954,722 A | 9/1999 | Bono | |
| 5,964,763 A | 10/1999 | Incavo | |
| 5,967,046 A | 10/1999 | Muller | |
| 5,968,046 A | 10/1999 | Castleman | |
| 5,968,047 A | 10/1999 | Reed | |
| 5,989,254 A | 11/1999 | Katz | |
| 6,007,535 A | 12/1999 | Rayhack et al. | |
| 6,010,503 A | 1/2000 | Richelsoph | |
| 6,010,505 A | 1/2000 | Asche et al. | |
| 6,022,350 A | 2/2000 | Ganem | |
| 6,053,917 A | 4/2000 | Sherman et al. | |
| 6,096,040 A | 8/2000 | Esser | |
| 6,123,709 A | 9/2000 | Jones | |
| 6,129,730 A | 10/2000 | Bono et al. | |
| 6,146,384 A | 11/2000 | Lee et al. | |
| 6,152,927 A | 11/2000 | Farris et al. | |
| 6,183,475 B1 | 2/2001 | Lester et al. | |
| 6,197,028 B1 | 3/2001 | Ray et al. | |
| 6,206,881 B1 | 3/2001 | Frigg et al. | |
| 6,221,073 B1 | 4/2001 | Weiss et al. | |
| D443,060 S | 5/2001 | Benirschke et al. | |
| 6,228,285 B1 | 5/2001 | Wang et al. | |
| 6,231,576 B1 | 5/2001 | Frigg et al. | |
| 6,235,033 B1 | 5/2001 | Brace et al. | |
| 6,235,034 B1 | 5/2001 | Bray | |
| 6,238,395 B1 | 5/2001 | Bonutti | |
| 6,241,736 B1 | 6/2001 | Sater et al. | |
| 6,248,109 B1 | 6/2001 | Stoffella | |
| 6,258,089 B1 | 7/2001 | Campbell et al. | |
| 6,270,499 B1 | 8/2001 | Leu et al. | |
| 6,283,969 B1 | 9/2001 | Grusin et al. | |
| 6,290,703 B1 | 9/2001 | Ganem | |
| 6,322,562 B1 | 11/2001 | Wolter | |
| 6,331,179 B1 * | 12/2001 | Freid et al. | 606/288 |
| 6,355,041 B1 | 3/2002 | Martin | |
| 6,355,043 B1 | 3/2002 | Adam | |
| 6,358,250 B1 | 3/2002 | Orbay | |
| 6,364,882 B1 | 4/2002 | Orbay | |
| 6,379,359 B1 | 4/2002 | Dahners | |
| 6,383,186 B1 | 5/2002 | Michelson | |
| 6,409,768 B1 | 6/2002 | Tepic et al. | |
| 6,440,135 B2 | 8/2002 | Orbay et al. | |
| 6,454,769 B2 | 9/2002 | Wagner et al. | |
| 6,454,770 B1 | 9/2002 | Klaue | |
| 6,458,133 B1 | 10/2002 | Lin | |
| 6,468,278 B1 | 10/2002 | Muckter | |
| 6,508,819 B1 | 1/2003 | Orbay | |
| 6,527,775 B1 | 3/2003 | Warburton | |
| 6,540,748 B2 | 4/2003 | Lombardo | |
| 6,595,993 B2 | 7/2003 | Donno et al. | |
| 6,599,290 B2 | 7/2003 | Bailey et al. | |
| 6,602,255 B1 | 8/2003 | Campbell et al. | |
| 6,623,486 B1 | 9/2003 | Weaver et al. | |
| 6,626,908 B2 | 9/2003 | Cooper et al. | |
| 6,645,212 B2 | 11/2003 | Goldhahn et al. | |
| 6,669,700 B1 | 12/2003 | Farris et al. | |
| 6,679,883 B2 | 1/2004 | Hawkes et al. | |
| 6,692,503 B2 | 2/2004 | Foley et al. | |
| 6,706,046 B2 | 3/2004 | Orbay et al. | |
| 6,712,820 B2 | 3/2004 | Orbay | |
| 6,719,758 B2 | 4/2004 | Beger et al. | |
| 6,730,090 B2 | 5/2004 | Orbay et al. | |
| 6,730,091 B1 | 5/2004 | Pfefferle et al. | |
| 6,755,831 B2 | 6/2004 | Putnam | |
| 6,761,719 B2 | 7/2004 | Justis et al. | |
| 6,767,351 B2 | 7/2004 | Orbay et al. | |
| 6,780,186 B2 | 8/2004 | Errico et al. | |
| 6,866,665 B2 | 3/2005 | Orbay | |
| 6,926,720 B2 | 8/2005 | Castaneda | |
| 6,955,677 B2 | 10/2005 | Dahners | |
| 6,974,461 B1 | 12/2005 | Wolter | |

| | | | |
|---|---|---|---|
| 7,090,676 B2 | 8/2006 | Huebner et al. | |
| 7,153,309 B2 | 12/2006 | Huebner et al. | |
| 7,905,909 B2 | 3/2011 | Orbay et al. | |
| 2001/0001119 A1 | 5/2001 | Lombardo | |
| 2001/0011172 A1 | 8/2001 | Orbay et al. | |
| 2001/0021851 A1 | 9/2001 | Eberlein et al. | |
| 2002/0032446 A1 | 3/2002 | Orbay | |
| 2002/0049445 A1 | 4/2002 | Hall, IV et al. | |
| 2002/0058939 A1 | 5/2002 | Wagner et al. | |
| 2002/0058941 A1 | 5/2002 | Clark et al. | |
| 2002/0111629 A1 | 8/2002 | Phillips | |
| 2002/0147452 A1 | 10/2002 | Medoff et al. | |
| 2002/0151899 A1 | 10/2002 | Bailey et al. | |
| 2002/0156474 A1 | 10/2002 | Wack et al. | |
| 2003/0045880 A1 | 3/2003 | Michelson | |
| 2003/0078583 A1 | 4/2003 | Biedermann et al. | |
| 2003/0083661 A1 | 5/2003 | Orbay et al. | |
| 2003/0105461 A1 | 6/2003 | Putnam | |
| 2003/0135212 A1 | 7/2003 | Chow | |
| 2003/0153919 A1 | 8/2003 | Harris | |
| 2003/0216735 A1 | 11/2003 | Altarac et al. | |
| 2004/0030339 A1 | 2/2004 | Wack et al. | |
| 2004/0059334 A1 | 3/2004 | Weaver et al. | |
| 2004/0059335 A1 | 3/2004 | Weaver et al. | |
| 2004/0068319 A1 | 4/2004 | Cordaro | |
| 2004/0073218 A1 | 4/2004 | Dahners | |
| 2004/0097934 A1 | 5/2004 | Farris et al. | |
| 2004/0097950 A1 | 5/2004 | Foley et al. | |
| 2004/0102778 A1 | 5/2004 | Huebner et al. | |
| 2004/0111090 A1 | 6/2004 | Dahners | |
| 2004/0193163 A1 | 9/2004 | Orbay | |
| 2004/0260291 A1 | 12/2004 | Jensen | |
| 2005/0004574 A1 | 1/2005 | Muckter | |
| 2005/0010226 A1 | 1/2005 | Grady | |
| 2005/0080421 A1 | 4/2005 | Weaver et al. | |
| 2005/0085818 A1 | 4/2005 | Huebner | |
| 2005/0131413 A1 | 6/2005 | O'Driscoll et al. | |
| 2005/0154392 A1 | 7/2005 | Medoff et al. | |
| 2005/0165400 A1 | 7/2005 | Fernandez | |
| 2005/0187551 A1 | 8/2005 | Orbay et al. | |
| 2005/0238459 A1 | 10/2005 | Levey | |
| 2006/0004362 A1 | 1/2006 | Patterson | |
| 2006/0004462 A1 | 1/2006 | Gupta | |
| 2006/0009771 A1 | 1/2006 | Orbay | |
| 2006/0015101 A1 | 1/2006 | Warburton et al. | |
| 2007/0088360 A1 | 4/2007 | Orbay et al. | |

FOREIGN PATENT DOCUMENTS

| | | |
|---|---|---|
| CN | 1379642 A | 11/2002 |
| DE | 3301298 | 2/1984 |
| DE | 4004941 | 8/1990 |
| DE | 19542116 A | 5/1997 |
| DE | 19629011 | 1/1998 |
| DE | 9321544 U1 | 10/1999 |
| DE | 4343117 C2 | 11/1999 |
| DE | 20200705 | 3/2002 |
| EP | 0451427 A1 | 5/1990 |
| EP | 0382256 A1 | 8/1990 |
| EP | 0689800 | 1/1996 |
| EP | 1250892 | 10/2002 |
| EP | 1996120 | 12/2008 |
| FR | 2233973 | 1/1975 |
| FR | 2405062 | 5/1979 |
| FR | 2855391 | 12/2004 |
| JP | 5-501666 | 4/1993 |
| JP | 7-10734 | 3/1995 |
| JP | 9504213 | 4/1997 |
| JP | 11-000337 | 1/1999 |
| JP | 11-47170 | 2/1999 |
| JP | 2000-189436 | 7/2000 |
| JP | 200189438 | 7/2000 |
| JP | 2003-210479 | 7/2003 |
| JP | 2003-245283 | 9/2003 |
| JP | 2004-049633 | 2/2004 |
| WO | WO97/47251 | 12/1997 |
| WO | WO00/04836 A1 | 2/2000 |
| WO | WO00/36984 | 6/2000 |
| WO | WO00/66011 | 11/2000 |
| WO | WO01/12081 | 2/2001 |
| WO | WO01/19267 A | 3/2001 |
| WO | WO01/56452 | 8/2001 |
| WO | WO2004/032751 | 4/2004 |
| WO | WO2004/096067 | 11/2004 |

OTHER PUBLICATIONS

ACE Medical Company, Curves in All the Right Places, ACE Symmetry Titanium Upper Extremity Plates, 1996.

"Advances in Distal Radius Fracture Management (D)," transcript of American Academy of Orthopaedic Surgeons 2001 Conference, pp. 134-151, Feb. 28, 2001.

Berger, Richard A., et al., Distal Radioulnar Joint Instability, Orthopedic Procedures, 2004, p. 337-354, vol. 1, Lippincott Williams & Wilkins.

Chung, Kevin C., et al., Treatment of Unstable Distal Radial Fractures with the Volar Locking Plating System, J. Bone Joint Surg. Am., 2006; p. 2687-2694, vol. 88.

The Distal Radius Plate Instrument and Implant Set; Technical Guide, Synthes, Paoli, PA; (1995).

Moftakhar, Roham, M.D. and Trost, Gregory R., M.D., "Anterior Cervical Plates: A Historical Perspective", Jan. 2004, pp. 1-5.

Nelson, "Volar Plating with Anatomic Placement and Fixed-Angle Screws", Quick Reference Guide for Contours VPS Volar Plate System by ORTHOFIX, May 2005, www.orthofix.com.

Nelson, David L., MD, Internal Fixation for the Distal Radius, eRadius, International Distal Radius Fracture Study Group, last updated Jan. 28, 2006, www.eradius.com/infix.htm.

"Numelock II Polyaxial Locking System," Stryker Corporation, brochure.

Polyaxial and Monoaxial Spinal Screws, XIA.TM. Spinal System, www.osteonics.com/osteonics/spine/xia2.html, Jun. 25, 2002.

Putnam, D. M.D., "Repair and Rehabilitation of Distal Fractures: The Role of Subchondral Fixation" at pp. 144-147.

"SCS /D Distal Radius Plate System: Dorsal", Avanta, 1997.

"SCS /V Distal Radius Plate: Volar", Avanta, 1998.

Smith, Dean W., MD, et al., Volar Fixed-Angle Plating of the Distal Radius, J. Am. Acad. Orth. Surg., Jan./Feb. 2005, p. 28-36, vol. 13, No. 1.

"SMARTLock Locking Screw Technology," Stryker Corporation, website description, 2004, www.stryker.lcom.

Summary of Safety and Effectiveness Information for Synthes Condylar Buttress Plates; Synthes USA (Approx. Jul. 29, 1998).

Synthes-Stratec Annual Report, 2001.

The Titanium Distal Radius Plate; Technique Guide, Synthes, Paoli, PA (1996).

"Universal Distal Radius System", Stryker Corporation, website description, 2004, www.stryker.com.

"Val Plate (Volar Angle Locking) for Distal Radius Fractures", US Implants, brochure.

"Volar Peg Plate Insertion Technique", Trimed, Inc., brochure.

"Volar Radius Plate with Angular Stability", I.T.S. (Implant Technology Systems), 510(k) Summary of Safety and Effectiveness, Feb. 6, 2004.

"Volare Winkelstabile Radiusplatte", I.T.S. (Implant Technology Systems), Spectromed, brochure, 2005, Austria.

* cited by examiner

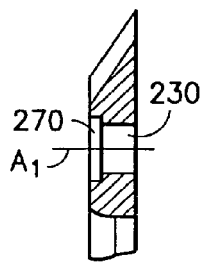
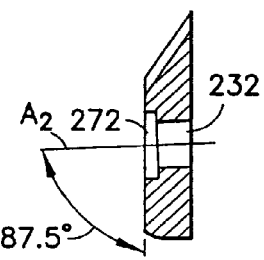
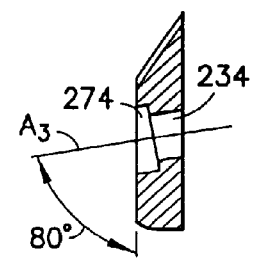
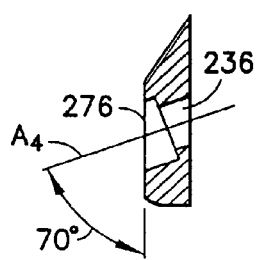
FIG.16  FIG.17  FIG.18  FIG.19
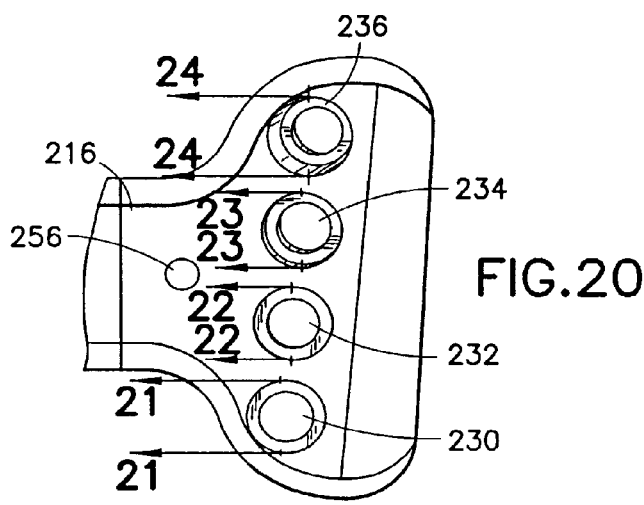
FIG.20
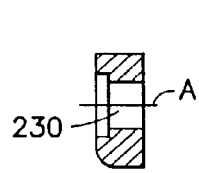
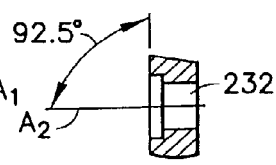
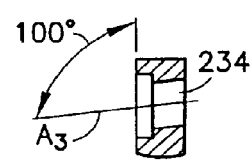
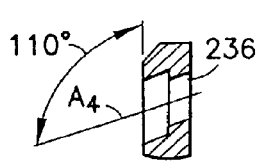
FIG.21  FIG.22  FIG.23  FIG.24

VOLAR FIXATION SYSTEM AND METHODS OF USING THE SAME

This application is a continuation of U.S. Ser. No. 11/181,354, filed Jul. 14, 2005, now abandoned which is a continuation of U.S. Ser. No. 10/762,695, filed Jan. 22, 2004, now abandoned which is a continuation-in-part of U.S. Ser. No. 10/315,787, filed Dec. 10, 2002, now U.S. Pat. No. 6,706,046 which is a continuation-in-part of U.S. Ser. No. 10/159,611, filed May 30, 2002, now U.S. Pat. No. 6,730,090 which is a continuation-in-part of U.S. Ser. No. 09/735,228, filed Dec. 12, 2000 and now issued as U.S. Pat. No. 6,440,135, which is a continuation-in-part of U.S. Ser. No. 09/524,058, filed Mar. 13, 2000 and now issued as U.S. Pat. No. 6,364,882, and U.S. Ser. No. 09/495,854, filed Feb. 1, 2000 and now issued as U.S. Pat. No. 6,358,250, the complete disclosures of which are hereby incorporated by reference herein.

BACKGROUND OF THE INVENTION

1. Field of the Invention

This invention relates broadly to surgical devices. More particularly, this invention relates to a bone fixation system, and particularly to a fixation system adapted to fixate a distal radius fracture.

2. State of the Art

Referring to FIG. 1, a Colles' fracture is a fracture resulting from compressive forces being placed on the distal radius 10, and which causes backward displacement of the distal fragment 12 and radial deviation of the hand at the wrist 14. Often, a Colles' fracture will result in multiple bone fragments 16, 18, 20 which are movable and out of alignment relative to each other. If not properly treated, such fractures result in permanent wrist deformity. It is therefore important to align the fracture and fixate the bones relative to each other so that proper healing may occur.

Alignment and fixation are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time consuming procedure. Moreover, unless the bracing is quite complex, the fracture may not be properly stabilized. Plating utilizes a stabilizing metal plate typically against the dorsal side of the bones, and a set of parallel pins extending from the plate into the holes drilled in the bone fragments to provide stabilized fixation of the fragments. However, the currently available plate systems fail to provide desirable alignment and stabilization.

SUMMARY OF THE INVENTION

It is therefore an object of the invention to provide an improved fixation and alignment system for a Colles' fracture.

It is another object of the invention to provide a volar fixation system which desirably aligns and stabilizes multiple bone fragments in a distal radial fracture to permit proper healing.

In accord with these objects, which will be discussed in detail below, a volar fixation system is provided which generally includes a T-shaped plate intended to be positioned against the volar side of the radial bone, a plurality of bone screws for securing the plate along a non-fractured portion of the radial bone, and a plurality of bone pegs which extend from the plate and into bone fragments of a Colles' fracture.

The plate is generally a T-shaped plate defining an elongate body, a head portion angled relative to the body, a first side which is intended to contact the bone, and a second side opposite the first side. The body portion includes a plurality of countersunk screw holes for the extension of the bone screws therethrough. The head portion includes a plurality of threaded peg holes for receiving the pegs therethrough. According to a first embodiment, the peg holes are preferably non-linearly arranged. According to a second embodiment, the peg holes are preferably linearly arranged. In either embodiment, the peg holes are positioned increasingly distal in a medial to lateral direction along the second side. According to a preferred aspect of the invention, axes through the holes are oblique relative to each other, and are preferably angled relative to each other in two dimensions. The pegs having a threaded head and a relatively smooth cylindrical shaft.

The system preferably also includes a guide plate which temporarily sits on top of the volar plate and includes holes oriented according to the axes of the peg holes for guiding a drill into the bone fragments at the required orientation. The volar plate and guide plate are also preferably provided with mating elements to temporarily stabilize the guide plate on the volar plate during the hole drilling process.

In use, the volar plate is positioned with its first side against the volar side of the radius and bone screws are inserted through the bone screw holes into the radius to secure the volar plate to the radius. The bone fragments are then aligned and the guide plate is positioned on the second side of the volar plate. A drill, guided by guide holes in the guide plate, drills holes into the bone fragments, and the guide plate is then removed.

The pegs are then inserted through the peg holes and into the holes in the bone, and the heads of the pegs are threadably engaged in the volar plate. The volar fixation system thereby secures the bone fragments in their proper orientation.

Additional objects and advantages of the invention will become apparent to those skilled in the art upon reference to the detailed description taken in conjunction with the provided figures.

BRIEF DESCRIPTION OF THE DRAWINGS

FIGS. 16-19 are section views across line 16-16, 17-17, 18-18, and 19-19, respectively in FIG. 15;

FIG. 20 is second partial top view of the head portion of the left hand volar plate according to the second embodiment of the volar fixation system of the invention; and FIGS. 21-24 are section views across line 21-21, 22-22, 23-23, and 24-24, respectively in FIG. 20.

DETAILED DESCRIPTION OF THE PREFERRED EMBODIMENTS

Figure 1:
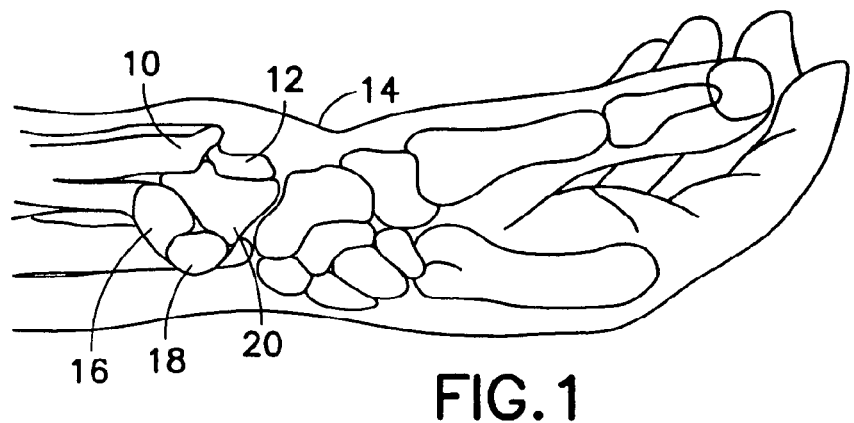
FIG. 1 is an illustration of an extremity subject to a Colles' fracture.
Figure 2:
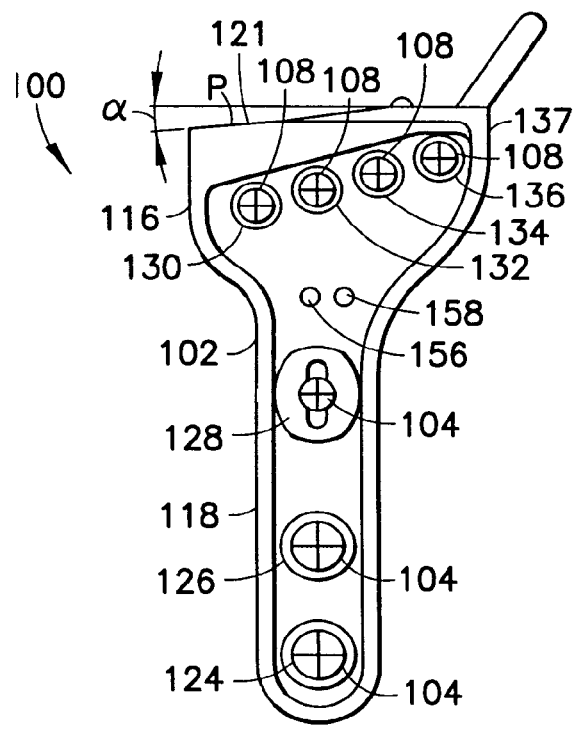
FIG. 2 is a top volar view of a right hand volar fixation system according to a first embodiment of the invention.
Figure 3:
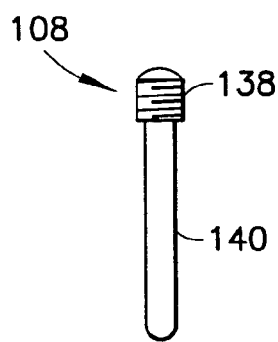
FIG. 3 is a side view of a bone peg according to the first embodiment of the volar fixation system of the invention.
Figure 4:
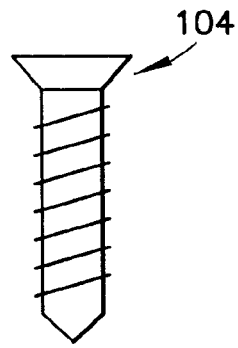
FIG. 4 is a side view of a bone screw of the volar fixation system of the invention.

Turning now to FIGS. 2 through 4, a first embodiment of a volar fixation system 100 for aligning and stabilizing multiple bone fragments in a Colles' fracture generally includes a substantially rigid T-shaped plate 102 intended to be positioned against the volar side of the radial bone, a plurality of preferably self-tapping bone screws 104 for securing the plate 102 along a non-fractured portion of the radial bone, and a plurality of bone pegs 108 which extend from the plate 102 and into bone fragments of a Colles' fracture.

Figure 5:
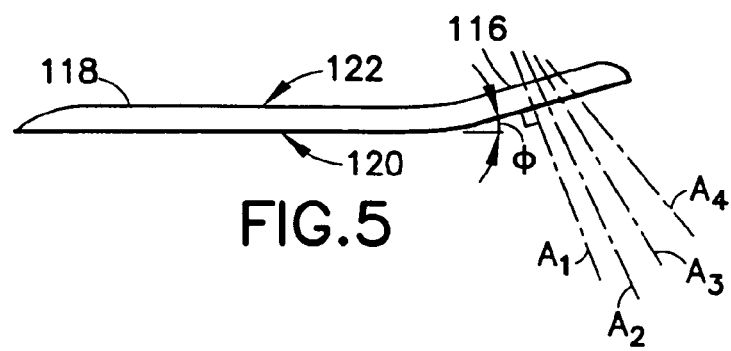
FIG. 5 is a side view of the right hand volar plate of the volar fixation system according to the first embodiment of the invention.
Figure 6:
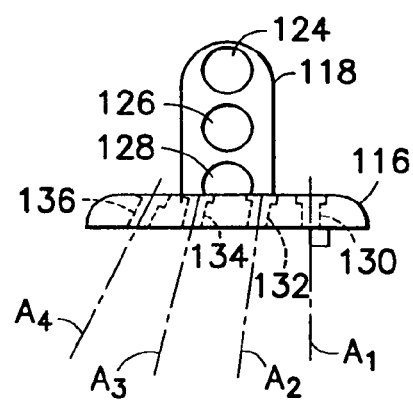
FIG. 6 is a front end view of the right hand volar plate of the volar fixation system according to the first embodiment of the invention.

Referring to FIGS. 2, 5 and 6, more particularly, the T-shaped plate 102 defines a head portion 116, an elongate body portion 118 angled relative to the head portion, a first side 120 which is intended to contact the bone, and a second side 122 opposite the first side. The first side 120 at the head portion is preferably planar, as is the first side at the body portion. As the head portion and body portion are angled relative to each other, the first side preferably defines two planar portions. The angle Ø between the head portion 116 and the body portion 118 is preferably approximately 18° and bent at a radius of approximately 1.00 inch (FIG. 5). The distal edge 121 of the head portion 116 is preferably angled proximally toward the medial side at an angle, e.g., 5°, relative to a line P, which is perpendicular to the body portion. The head portion 116 preferably has a width of 0.913 inch and a greatest proximal-distal dimension (i.e., from the corner of angle to the body portion) of approximately 0.69 inch, and the body portion preferably has a width of 0.375 inch and a length of 1.40 inches. The plate 102 preferably has a thickness of approximately 0.098 inch. The plate 102 is preferably made from a titanium alloy, such as Ti-6A-4V.

The body portion 118 includes three preferably countersunk screw holes 124, 126, 128 for the extension of the bone screws 104 therethrough. The first screw hole 124 has a center preferably 0.235 inch from the end of the body portion, the second screw hole 126 has a center preferably 0.630 inch from the end of the body portion, and the third screw hole 128 is preferably generally elliptical (or oval) and defines foci-like locations at 1.020 inches and 1.050 inches from the end of the body portion. The head portion 116 includes four threaded peg holes 130, 132, 134, 136 for individually receiving the pegs 108 therethrough. According to a first preferred aspect of the first embodiment of the invention, the peg holes 130, 132, 134, 136, preferably 0.100 inch in diameter, are preferably non-linearly arranged along the head portion 116, and are provided such that the adjacent peg holes are provided further distally in a medial to lateral direction along the second side. More particularly, according to a preferred aspect of the first embodiment of the invention, the peg holes are preferably arranged along a parabolic curve, with the center of peg hole 130 located approximately 0.321 inch proximal line P and approximately 0.719 inch medial of the lateral edge 137 of the head portion, the center of peg hole 132 located approximately 0.296 inch proximal line P and approximately 0.544 inch medial of the lateral edge 137, the center of peg hole 134 located approximately 0.250 inch proximal line P and approximately 0.369 inch medial of the lateral edge 137, and the center of peg hole 136 located approximately 0.191 inch proximal line P and approximately 0.194 inch medial of the lateral edge 137.

In addition, according to a second preferred aspect of the first embodiment of the invention, the peg holes define fixed central axes $A_1, A_2, A_3, A_4$ which are oblique (not parallel) relative to each other, and more preferably are angled in two dimensions (medial/lateral and proximal/distal) relative to each other; i.e., the pegs once inserted into the peg holes are also angled in two dimensions relative to each other. More particularly, the first axis $A_1$ of the first peg hole 130 (that is, the most proximal and medial peg hole) is preferably directed normal to the first side 120 of the head portion 116. The axis $A_2$ of the adjacent peg hole 132, i.e., the second axis, is preferably angled approximately 1-7° distal and lateral relative to the first axis $A_1$, and more preferably approximately 2.5° distal and lateral relative to the first axis $A_1$. The axis $A_3$ of the peg hole 134 laterally adjacent the second peg hole 132, i.e., the third axis, is preferably angled approximately 7-13° distal and lateral relative to the first axis $A_1$, and more preferably approximately 10° distal and lateral relative to the first axis $A_1$. The axis $A_4$ of the peg hole 134 laterally adjacent the third peg hole 132, i.e., the fourth axis, is preferably angled approximately 10-30° distal and lateral relative to the first axis $A_1$, and more preferably approximately 20° distal and lateral relative to the first axis $A_1$. The second side of the head portion 116, distal of the peg holes 130, 132, 134, 136 is preferably beveled.

Referring back to FIG. 3, the pegs 108, preferably approximately 0.872 inch in length, each have a threaded head 138 adapted to threadably engage the threads about the peg holes 130, 132, 134, 136, and have a relatively smooth non-threaded cylindrical shaft 140. The shafts 140 are preferably approximately 0.0675 inch in diameter and 0.765 inch in length. Such dimensions permit the pegs to adequately support the bone fragments such that the bone is able to heal correctly. The pegs 108 are also preferably made from titanium alloy, and may be coated in a ceramic, e.g., titanium nitride, to provide a bone interface which will not adversely affect bone healing.

Figure 7:
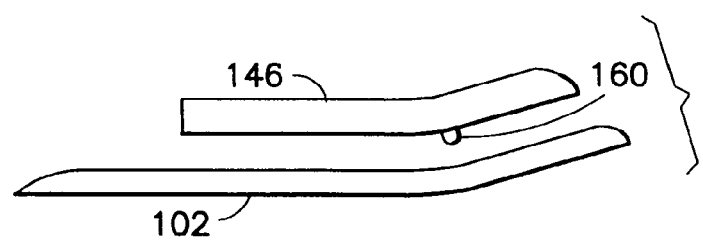
FIG. 7 is an exploded side view of the right hand volar plate and guide plate according to the first embodiment of the fixation system of the invention.
Figure 8:
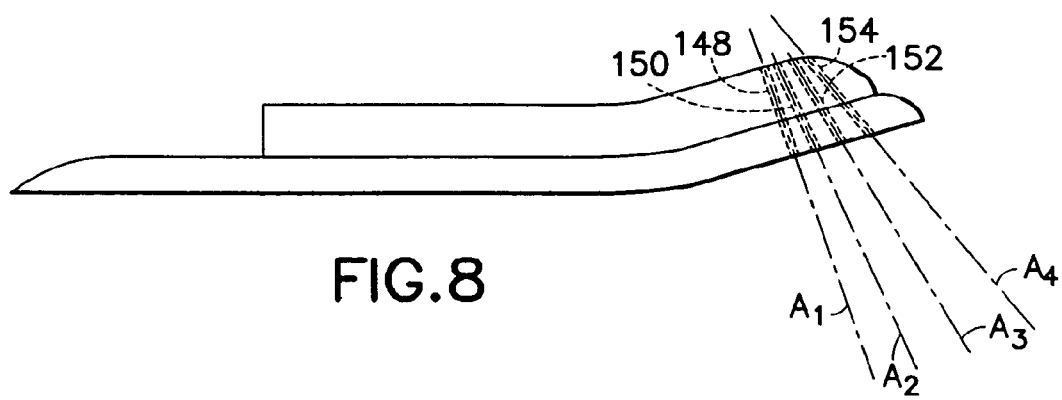
FIG. 8 is a side view of the guide plate positioned on the right hand volar plate to provide drill guide paths in accord with the invention.
Figure 9:
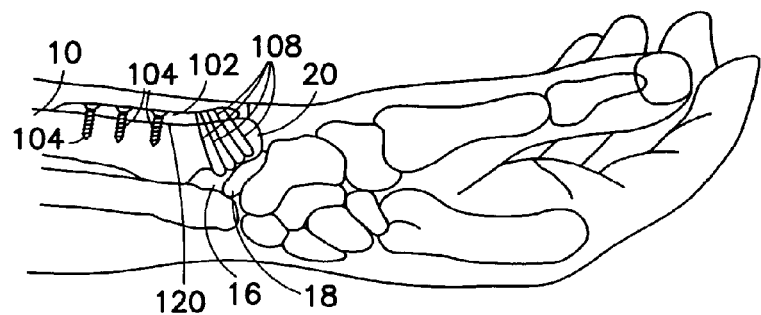
FIG. 9 is an illustration of the first embodiment of the volar fixation system provided in situ aligning and stabilizing a Colles' fracture.

Turning now to FIGS. 7 and 8, the system 100 preferably also includes a guide plate 146 which temporarily sits on the second side 122 of the volar plate 102 and includes guide holes 148, 150, 152, 154 (illustrated in overlapping section in FIG. 8) oriented according to the axes $A_1$, $A_2$, $A_3$, $A_4$ of the peg holes for guiding a drill into the bone fragments at the required orientation. That is, the guide holes together with the peg holes define a drill guide path along the axes with sufficient depth to accurately guide a drill (not shown) to drill holes at the desired pin orientations. The volar plate 102 and guide plate 146 are also preferably provided with mating elements, such as a plurality of holes 156, 158 on the second side of the volar plate (FIG. 2), and a plurality of protuberances 160 on the mating side of the guide plate (FIG. 7), to temporarily stabilize the guide plate on the volar plate during the hole drilling process.

Referring to FIGS. 2 through 9, in use, the volar plate 102 is positioned with its first side 120 against the volar side of the radius. Bone screws 104 (either self-tapping or inserted with the aid of pre-drilled pilot holes) are inserted through the bone screw holes 124, 126, 128 into the radius bone 10 to secure the volar plate 102 to the radius. The bone fragments 16, 18, 20 are then aligned with the radius 10. Next, the guide plate 146 is positioned on the second side of the volar plate. A drill, guided by a guide path formed by the peg holes and the guide holes, drills holes into and between the bone fragments 16, 18, 20 (and possibly also a portion of the integral radius, depending upon the particular location and extent of the fracture), and the guide plate is then removed. The pegs 108 are then inserted through the peg holes 130, 132, 134, 136 and into the holes drilled into the fragments, and the heads of the pegs are threadably engaged in the volar plate. The pegs 108, extending through the fixed orientation oblique-axis peg holes 130, 132, 134, 136, and threadedly engaged to the plate are positioned in a fixed angular relationship relative to the head portion of the plate and extend immediately below the subchondral bone of the radius and support the bone fragments for proper healing. The volar fixation system thereby secures the bone fragments in their proper orientation.

Figure 10:
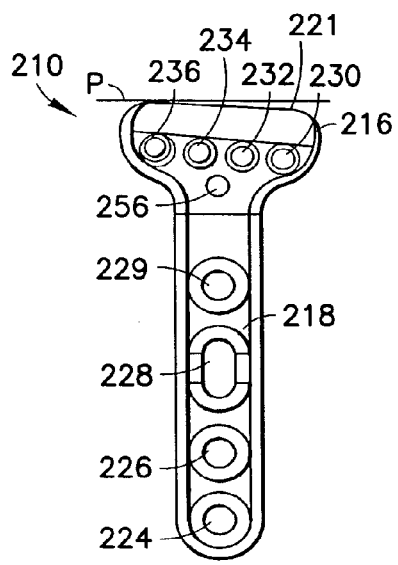
FIG. 10 is a top volar view of a left hand volar fixation system according to the second embodiment of the invention.
Figure 11:
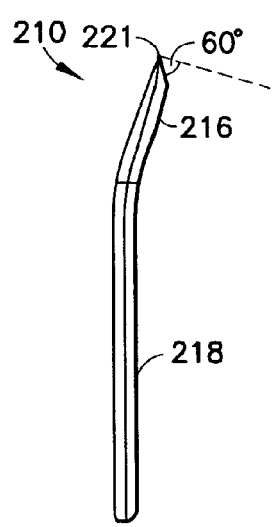
FIG. 11 is a lateral side view of the left hand volar fixation system according to the second embodiment of the invention.
Figure 12:
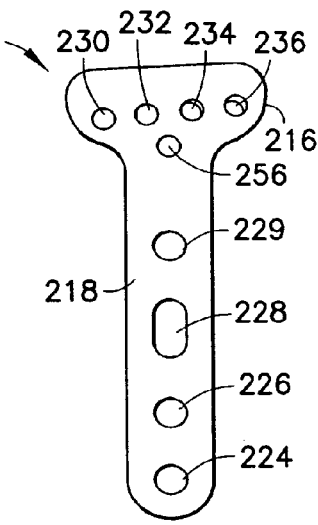
FIG. 12 is a bottom view of the left hand volar fixation system according to the second embodiment of the invention.

Referring to FIGS. 10-12, a second embodiment of a volar plate 210, substantially similar to the first embodiment (with like parts having numbers incremented by 100) and used in substantially the same manner as the first embodiment is shown. The plate 210 preferably has a length of approximately 2.35 inches, which is approximately 0.35 inch greater than in the first embodiment. This additional length accommodates an extra bone screw hole 229 in the body of the volar plate such that the volar plate preferably includes four bone screw holes 224, 226, 228, 229. The additional bone screw in screw hole 229 increases plate stability over the three holes of the first embodiment. The plate 210 preferably tapers in thickness from the body portion 218 to the head portion 216. A preferred taper provides a proximal body portion 218 thickness of approximately 0.098 inch and head portion 216 thickness of approximately 0.078 inch. The taper decreases the thickness of the head portion 216 relative to the body such that the weight of the volar plate is reduced and an improved tendon clearance is provided. The distal edge of the head portion 216 has an increased taper (preferably approximately 60° relative to a line normal to the head) to a distal edge 221. The edge 221 is broken (i.e., made blunt) to prevent irritation or disturbance to the surrounding anatomy.

The head portion 216 includes four threaded peg holes 230, 232, 234, 236 for individually receiving pegs 208 therethrough (FIGS. 13 and 14), and a guide hole 256 for alignment of a guide plate. According to a preferred aspect of the second embodiment of the invention, the peg holes 230, 232, 234, 236, preferably 0.100 inch in diameter, are preferably linearly arranged along the head portion 216, and are provided such that the adjacent peg holes are provided further distally in a medial to lateral direction along the first and second sides. Referring to FIG. 15, more particularly, according to a preferred dimensions of the second embodiment of the invention, the center of peg hole 230 is located approximately 0.321 inch proximal line P and approximately 0.750 inch medial of the lateral edge 237 of the head portion, the center of peg hole 232 is located approximately 0.306 inch proximal line P and 0.557 inch medial of the lateral edge 237, the center of peg hole 234 is located approximately 0.289 inch proximal line P and approximately 0.364 inch medial of the lateral edge 237, and the center of peg hole 236 is located approximately 0.272 inch proximal line P and approximately 0.171 inch medial of the lateral edge 237. As such, the distance from each of the peg holes to the distal edge 221 of the volar plate is relatively greater than in the first embodiment, and provides a preferred alignment with respect to the tapered distal edge 221.

Referring to FIGS. 15-24, in addition, as in the first embodiment, the peg holes define fixed central axes $A_1$, $A_2$, $A_3$, $A_4$ which are oblique relative to each other, and more preferably are angled in two dimensions (medial/lateral and proximal/distal) relative to each other; i.e., the pegs 208 once inserted into the peg holes are also angled in two dimensions relative to each other. More particularly, as in the first embodiment, the first axis $A_1$ of the first peg hole 230 is preferably directed normal (FIGS. 16 and 21) to the first side 220 of the head portion 216. The axis $A_2$ of peg hole 232 is preferably angled approximately 1-7° distal (FIG. 17) and approximately 1-7° lateral (FIG. 22) relative to the axis $A_1$, and more preferably approximately 2.5° both distal and lateral relative to axis $A_1$. The axis $A_3$ of peg hole 234 is preferably angled approximately 7-13° distal (FIG. 18) and approximately 7-13° lateral (FIG. 23) relative to axis $A_1$, and more preferably approximately 10° both distal and lateral relative to axis $A_1$. Axis $A_4$ of the peg hole 234 is preferably angled approximately 10-30° distal (FIG. 19) and approximately 10-30° lateral (FIG. 24) relative to axis $A_1$, and more preferably approximately 20° both distal and lateral relative to axis $A_1$.

Referring to FIGS. 13 and 16-19, each of the peg holes has a countersunk portion 270, 272, 274, 276, respectively, for receiving the head 238 of peg 208. Countersunk portions 270, 272 are each preferably approximately 0.030 inch deep and threaded according to the head of the pegs, as described below. Countersunk portion 274 is preferably approximately 0.042 inch deep and likewise threaded. Countersunk portion 276 is preferably approximately 0.056 inch deep and also threaded. The respective depths of the countersunk portions are adapted to better accommodate the heads 238 of the pegs 208 relative to the respective axes of the peg holes.

Figures 13, 14:
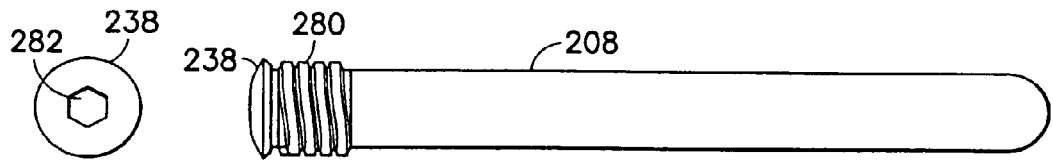
FIG. 13 is an enlarged side elevation of a bone peg according to the second embodiment of the volar fixation system of the invention.
FIG. 14 is a proximal end view of the bone peg of FIG. 13.
Figure 15:
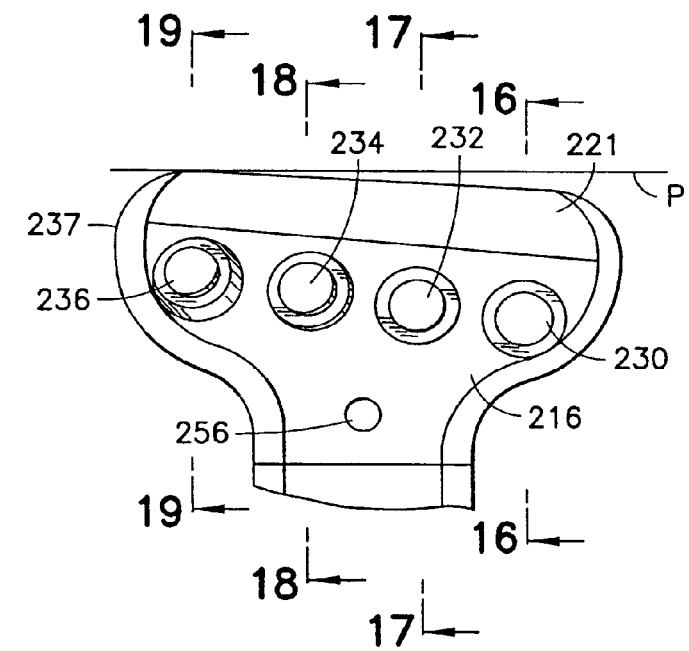
FIG. 15 is first partial top view of the head portion of the left hand volar plate according to the second embodiment of the volar fixation system of the invention.

Referring to FIGS. 13 and 14, the pegs 208, preferably approximately 0.872 inch in length, each have a threaded head 238 adapted to threadably engage threads about the peg holes 230, 232, 234, 236, and have a relatively smooth non-threaded cylindrical shaft 240. The heads 238 preferably include a no. 5 thread 280 at a count of 44 per inch. In addition, the heads 238 are rounded and include a hex socket 282 to facilitate stabilized threading into the peg holes. This design accommodates the reduced thickness of the volar plate at the head portion 216. The shafts 240 are preferably approximately 0.0792 inch (2 mm) in diameter and 0.765 inch in length. Such dimensions permit the pegs to adequately support the bone fragments such that the bone is able to heal correctly. The pegs 208 are also preferably made from titanium alloy, and may be 'tiodized' to provide a strong finish which does not adversely affect bone healing.

There have been described and illustrated herein embodiments of a volar fixation system and a method of aligning and stabilizing a Colles' fracture. While particular embodiments of the invention have been described, it is not intended that the invention be limited thereto, as it is intended that the invention be as broad in scope as the art will allow and that the specification be read likewise. Thus, while particular materials for the elements of the system have been disclosed, it will be appreciated that other materials may be used as well. In addition, while a particular numbers of screw holes in the volar plates and bone screws have been described, it will be understood another number of screw holes and screws may be provided. Further, fewer screws than the number of screw holes may be used to secure to the volar plate to the radius. Also, fewer or more peg holes and bone pegs may be used, preferably such that at least two pegs angled in two dimensions relative to each other are provided. Moreover, while in the first embodiment it is preferred that the peg holes lie along a parabolic curve, it will be appreciated that they can lie along another curve. In addition, while a particular preferred angle between the head portion and body portion has been disclosed, other angles can also be used. Furthermore, while particular distances are disclosed between the peg holes and line P, it will be appreciated that the peg holes may be provided at other distances relative thereto. Moreover, while particular preferred medial/lateral and proximal/distal angles for the peg hole axes has been disclosed, it will be appreciated that yet other angles may be used in accord with the invention. Also, while a right-handed volar plate is described with respect to the first embodiment, and a left-handed volar plate is described with respect to the second embodiment, it will be appreciated that each embodiment may be formed in either a right- or left-handed model, with such alternate models being mirror images of the models described. In addition, aspects from each of the embodiments may be combined. It will therefore be appreciated by those skilled in the art that yet other modifications could be made to the provided invention without deviating from its spirit and scope as claimed.

The invention claimed is:

1. A method of stabilizing a fracture of a distal radius bone, the distal radius bone having subchondral bone that defines an articular surface with a concave curvature, the method comprising:
   a) with a rigid volar plate having a proximal body portion and a distal head portion, each of said body portion and said head portion provided with a bone contacting first surface and an opposite second surface, said head portion angled upward with respect to a plane containing said body portion when said bone contacting first surface of said body portion is facing downward, said head portion including at least three first holes arranged in a generally medial to lateral direction, each of said first holes defining a respective fixed central axis that is at a defined angle relative to a line normal to the first surface of said head portion, each said defined angle being at a unique number of degrees from the other of said first holes relative to said line normal, wherein a second of said first holes is angled at 1-7 degrees relative to a first of said first holes and said body portion including a plurality of second holes,
      positioning the bone contacting first surface of said body portion against the volar side of the radius bone;
   b) inserting at least one bone screw with a threaded shaft through the second holes and into the radius bone to secure the volar plate against the volar side of the radius bone;
   c) reducing the fracture;
   d) after reducing the fracture, inserting a first plurality of fracture stabilizing elements through said first holes in said head portion and into the volar side of the radius bone, each fracture stabilizing element having a head at which the fracture stabilizing element can be rigidly coupled to the plate and a shaft which extends into the radius bone, wherein when said head is rigidly coupled to said plate said shaft of each fracture stabilizing element can extend solely along the fixed central axis; and
   e) rigidly coupling said head of each of said first plurality of fracture stabilizing elements directly to said head portion of said plate such that said shafts of each of said first plurality of fracture stabilizing elements extend immediately below the subchondral bone of the radius bone and are in a fixed axial relationship relative to said head portion of said plate in which said shafts of said first plurality of fracture stabilizing elements extend divergently relative to each other from said bone contacting first surface of said plate in both a medial-lateral direction and a proximal-distal direction and together form a stabilizing construct for the subchondral bone.

2. A method according to claim 1, further comprising:
   before inserting said first plurality of fracture stabilizing elements, drilling into the radius bone to define bone holes for said shafts of said first plurality of fracture stabilizing elements.

3. A method according to claim 2, wherein:
   said drilling is performed through a plurality of guide holes situated above said second surface of said plate, each of said guide holes having a bore axis coaxial with a respective one of said fixed central axes.

4. A method according to claim 1, wherein:
   said volar plate includes four first holes.

5. The method of claim 1, wherein each fixed central axis is defined by an internal thread within said respective first hole, said head of each screw includes an external thread, and said rigid coupling includes threadedly engaging said external thread of said head with said internal thread of said hole.

6. A method of stabilizing a fracture of a distal radius having a volar side and a subchondral bone defining an articular surface, the method comprising:
   a) obtaining a rigid plate comprising a proximal body portion and a distal head portion, each of said body portion and said head portion comprising a bone contacting surface, said head portion angled upward with respect to a plane containing said body portion when said bone contacting first surface of said body portion is facing downward, said head portion including at least three holes arranged in a generally medial to lateral direction, each of said at least three holes having a fixed axis that is at a defined angle relative to a line normal to the first surface of said head portion, each said defined angle being at a unique number of degrees from the other of said at least three holes relative to said line normal, wherein a third of said at least three holes is angled at 7-13 degrees relative to a second of said at least three holes and said body portion including a plurality of holes;
   b) positioning the bone contacting surface of said body portion against the volar side of the radius;
   c) obtaining a first plurality of bone fasteners each comprising a threaded shaft and a head;

d) inserting at least one of the first plurality of bone fasteners through a hole in the body portion and into the volar side of the radius such that said threaded shaft engages the radius;
e) obtaining a second plurality of bone fasteners each comprising a shaft and a threaded head capable of being rigidly coupled to the plate;
f) after inserting at least one of said first plurality of bone fasteners, inserting the second plurality of bone fasteners through said holes in said head portion and into the volar side of the radius such that said shafts of the second plurality of bone fasteners extend immediately below the subchondral bone of the radius; and
g) rigidly coupling said heads of second plurality of bone fasteners to said head portion of said plate such that said shafts of the second plurality of bone fasteners are in a fixed angular relationship relative to said head portion of said plate in which said shafts of said second plurality of bone fasteners extends in a unique orientation relative to a line normal relative to said first surface of said head portion.

7. The method of claim 6, wherein said second bone fasteners comprises a peg.

8. A method of stabilizing a fracture of a distal radius having a volar side and a subchondral bone defining an articular surface, the method comprising:
a) obtaining a rigid plate comprising a proximal body portion and a distal head portion, each of said body portion and said head portion comprising a bone contacting surface, said head portion angled upward with respect to a plane containing said body portion when said bone contacting first surface of said body portion is facing downward, said head portion including at least three holes arranged in a generally medial to lateral direction, each of said at least three holes having a fixed axis that is at a defined angle relative to a line normal to the first surface of said head portion, each said defined angle being at a unique number of degrees from the other of said at least three holes relative to said line normal, wherein a second of said at least three holes is angled at 1-7 degrees relative to a first of said at least three holes wherein a third of said at least three holes is angled at 7-13 degrees relative to a second of said at least three holes and said body portion including a plurality of holes;
b) positioning the bone contacting surface of said body portion against the volar side of the radius;
c) obtaining a first plurality of bone anchors each comprising a threaded shaft and a head;
d) inserting at least one of the first plurality of bone anchors through a hole in the body portion and into the volar side of the radius such that said threaded shaft engages the radius;
e) obtaining a second plurality of bone anchors each comprising a shaft and a threaded head capable of being rigidly coupled to the plate;
f) after inserting at least one of said first plurality of bone anchors, inserting the second plurality of bone anchors through said holes in said head portion and into the volar side of the radius such that said shafts of the second plurality of bone anchors extend immediately below the subchondral bone of the radius; and
g) rigidly coupling said heads of second plurality of bone anchors to said head portion of said plate such that said shafts of the second plurality of bone anchors are in a fixed angular relationship relative to said head portion of said plate in which each said shafts of said second plurality of bone anchors extends in a unique orientation relative to a line normal relative to said first surface of said head portion.

9. The method of claim 8, wherein said second bone anchors comprises a peg.

* * * * *